US00PP13047P2

(12) United States Plant Patent
Heims

(10) Patent No.: US PP13,047 P2
(45) Date of Patent: Oct. 1, 2002

(54) PULMONARIA PLANT NAMED 'TREVI FOUNTAIN'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/545,925

(22) Filed: Apr. 10, 2000

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—Klarquist Sparkman, LLP

(57) ABSTRACT

A new and distinct hybrid of Pulmonaria plant characterized by a unique combination of long, slender foliage and cobalt-blue flowers.

1 Drawing Sheet

The present invention relates to a new and distinct hybrid of Pulmonaria, of the family Boraginaceae, which originated as a cross between an unpatented *Pulmonaria longifolia* plant named 'Bertram Anderson' (seed parent) and an unpatented *Pulmonaria vallarsae* plant named 'Margery Fish' (pollen parent). As the instant plant is the result of a cross between two different Pulmonaria species, no species designation is assigned.

This new Pulmonaria is the result of a controlled cross of the aforementioned plants in Canby, Oreg. This hybrid was selected from a large selection of seedlings. Seed and pollen parent plants were retained to observe habit and to compare with the instant plant. The new variety has been reproduced only by asexual propagation (division and tissue culture). Each of the progeny exhibits identical characteristics to the original plant.

This plant is characterized by the following:

1. Long slender leaves.
2. Large cobalt-blue flowers in spring.

Asexual propagation by division and tissue culture as done in Canby, Oreg., shows that the foregoing characteristics and distinctions come true to form and are established and transmitted through succeeding propagations.

BRIEF DESCRIPTION OF THE DRAWING

The drawing shows a two and a half year old Pulmonaria 'Trevi Fountain' plant growing in the ground in Portland, Oreg.

DETAILED PLANT DESCRIPTION

The following is a detailed description of the new Pulmonaria hybrid based on observations of two and a half year old field grown specimens in Canby, Oreg. The color descriptions are all based on The Royal Horticultural Society Colour Chart.

Foliage:
- *Type.*—Simple. Evergreen.
- *Shape.*—Lanceolate.
- *Length.*—15 to 20 cm.
- *Width.*—4 to 6 cm.
- *Petiole length.*—11.5 to 14.5 cm.
- *Margins.*—Entire-ciliolate.
- *Apex.*—Narrowly-acute.
- *Base.*—Attenuate.

- *Leaf texture.*—Setose.
- *Petiole texture.*—Setulose.
- *Leaf arrangement.*—Rosette.
- *Venation.*—Reticulate.

Plant size:
- *Height.*—31 to 35 cm.
- *Width.*—56 to 64 cm.

Flower:
- *Type.*—Perfect.
- *Shape.*—Salverform.
- *Size.*—9 mm from petal tip to petal tip.
- *Corolla.*—5 fused petals.
- *Calyx.*—5 fused sepals.
- *Ovary position.*—Partly inferior.
- *Carpel number.*—4.
- *Stamen number.*—5.
- *Inflorescence type.*—Forked cymes.
- *Inflorescence number per plant (2-year-old).*—40 to 50.
- *Flower number per inflorescence.*—20 to 30 with 5 to 10 open at any given time.
- *Peduncle width.*—4.5 mm tapering to 2 mm.
- *Peduncle texture.*—Setose.
- *Blooming height.*—25 cm.
- *Bloom period.*—Late February to late April.
- *Lastingness of the blooms.*—Each cyme blooms for about 3 weeks on the plant. Removal of spent cymes will induce secondary and tertiary bloom periods. This greatly extends the bloom period.
- *Fragrance.*—None.

Fruit:
- *Type.*—4 smooth nutlets, black and shiny, 3 mm by 2 mm.
- *Fertility.*—Fertile.

Plant habit: Clumping.
Disease: Powdery-mildew resistant.
Hardiness: USDA zones 4–9.

COLOR CHARACTERISTICS

Foliage:
- *Upper surface.*—RHS 137A Green Group.
- *Upper surface, spots.*—RHS 191C–D Greyed-Green Group.
- *Lower surface.*—RHS 191A Greyed-Green Group.

Petiole: RHS 146D Yellow-Green Group.

Flower:

*Petal.*—RHS 82A–B Purple-Violet Group intensifying to RHS 94A Violet-Blue Group with age.

*Sepal.*—RHS 147A Yellow-Green Group.

Peduncle: RHS 146B Yellow-Green Group.

Seed: RHS 202A Black Group.

DESCRIPTION OF PARENT PLANTS

The instant plant resulted from a cross between *Pulmonaria longifolia* 'Bertram Anderson', and *Pulmonaria vallarsae* 'Margery Fish'. *Pulmonaria longifolia* 'Bertram Anderson' has violet-blue flowers and dark green, long, slender leaves with silvery spots. The instant plant differs from *Pulmonaria longifolia* 'Bertram Anderson' in having cobalt-blue flowers and is more powdery-mildew resistant. *Pulmonaria vallarsae* 'Margery Fish' was selected for its powdery-mildew resistance and vigor. *Pulmonaria vallarsae* 'Margery Fish' has a compact form and pink flowers that turn blue as the flowers mature. The instant plant differs from *Pulmonaria vallarsae* 'Margery Fish' in having narrower, longer foliage and flowers that are held higher and retain their color better.

I claim:

1. A new and distinct hybrid of Pulmonaria plant substantially as shown and described, characterized by a unique combination of long, slender foliage and cobalt-blue flowers.

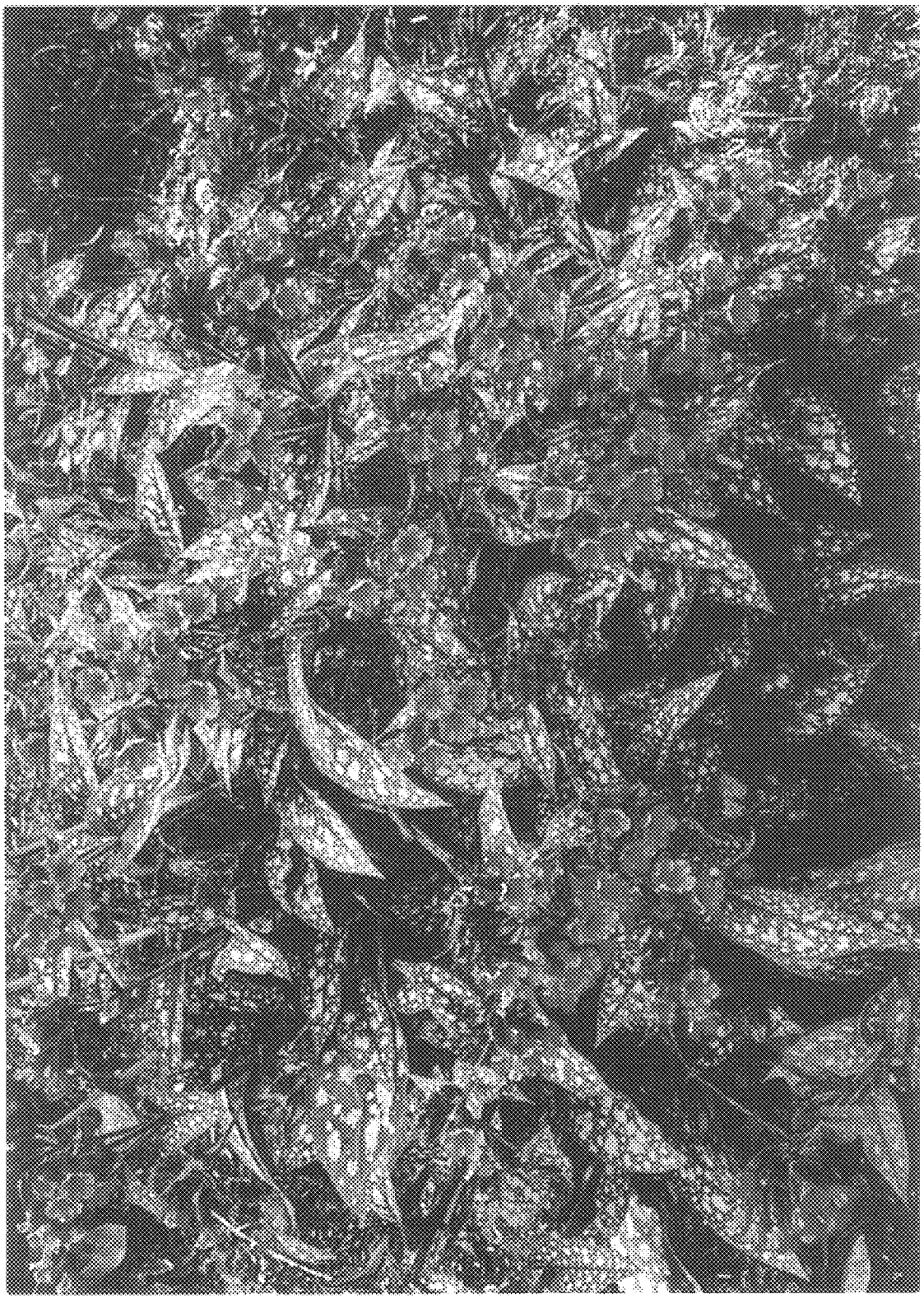

* * * * *